(12) United States Patent
Womack

(10) Patent No.: US 6,413,086 B1
(45) Date of Patent: Jul. 2, 2002

(54) INTERPROXIMAL GAUGE AND METHOD FOR DETERMINING A WIDTH OF A GAP BETWEEN ADJACENT TEETH

(76) Inventor: William R. Womack, 2519 E. Palo Verde Dr., Phoenix, AZ (US) 85016

( * ) Notice: Subject to any disclaimer, the term of this patent is extended or adjusted under 35 U.S.C. 154(b) by 0 days.

(21) Appl. No.: 09/943,835

(22) Filed: Aug. 30, 2001

(51) Int. Cl.[7] .............................................. A61C 19/04
(52) U.S. Cl. .............................. 433/72; 33/513; 33/562
(58) Field of Search ....................... 433/72, 75; 33/513, 33/514, 501.45, 562

(56) References Cited

U.S. PATENT DOCUMENTS

| | | | |
|---|---|---|---|
| 1,465,920 A | * | 8/1923 | Francis |
| 1,875,784 A | * | 9/1932 | Walker |
| 3,063,153 A | * | 11/1962 | Stites |
| 4,283,858 A | * | 8/1981 | Sobczak |
| D294,639 S | | 3/1988 | Croll |
| 5,044,951 A | | 9/1991 | Sheridan ...................... 433/72 |
| 5,617,644 A | * | 4/1997 | Bonelli |
| 5,927,299 A | * | 7/1999 | Rappoport |
| 5,975,893 A | | 11/1999 | Chishti et al. .................. 433/6 |

* cited by examiner

Primary Examiner—Ralph A. Lewis
(74) Attorney, Agent, or Firm—Jordan M. Meschkow; Lowell W. Gresham; Meschow & Gresham, P.L.C.

(57) ABSTRACT

An interproximal gauge (36) includes a plurality of blades (38), each having a key portion (40) and a handle (42) adjoining the key portion (40). The key portion (40) exhibits a predetermined thickness which is different for different ones of the blades (38) and is configured for placement in an interproximal gap (24) between adjacent teeth (26). The handle (42) includes notches (42) having numerical values representing the predetermined thickness of a particular one of the blades (38). Successive ones of the blades (38) are placed in the interproximal gap (24) and one of the blades (38) is selected having a predetermined thickness that is substantially equivalent to a width (28) of gap (24). The notches (42) are interpreted to determine the width (28) of the gap (24).

20 Claims, 3 Drawing Sheets

INTERPROXIMAL GAUGE AND METHOD FOR DETERMINING A WIDTH OF A GAP BETWEEN ADJACENT TEETH

TECHNICAL FIELD OF THE INVENTION

The present invention relates to the field of orthodontics. More specifically, the present invention relates to an interproximal gauge for the examination of the interproximal gap between adjacent teeth.

BACKGROUND OF THE INVENTION

One of the problems which exists in the practice of orthodontics is that of accurately measuring the interproximal gaps, or the spaces between adjacent teeth in the dental arches. The determination of the width of these interproximal gaps is desirable not only for restoration and cosmetic purposes, but also to develop treatment strategies that prevent foodstuff from wedging between the teeth and between the teeth and gum, that can cause discomfort, as well as potentially more severe periodontal disease.

Interproximal gaps may be naturally-occurring or mechanically-created. Mechanically-created interproximal gaps are formed by a reduction procedure, also referred to as stripping, reproximation, and slenderizing. During an interproximal reduction procedure, a small amount of enamel thickness on the surfaces of the teeth is removed to reduce the mesiodistal width and space requirements for the tooth. Interproximal reduction is typically employed to create space for faster/easier-orthodontic treatment.

Various types of devices are known in the field of orthodontics for measuring the width of interproximal gaps between adjacent teeth. Gauge plates having a variety of thicknesses have been used for insertion in interproximal gaps, in order to measure the width of a gap, or space, between adjacent teeth. These gauge plates, also known as dental contact gauges, are usually constructed of stainless steel and are provided with a grip portion, typically formed from a synthetic resin, which may be color-coded according to the thickness of the plate. Three types of gauge plates currently available are generally fifty microns (green grip), one hundred and ten microns (yellow grip) and one hundred and fifty microns (red grip) in thickness. In use, the gauge plates are inserted into the interproximal gap in order of plate thickness, from the thinner gauge plate to the thicker one, until the succeeding gauge plate cannot be inserted therein. The practitioner then estimates the width of the interproximal gap under investigation according to data printed in a table provided with the instruments.

The intent of the color-coded grip portion is to provide a quick visual determination of the thickness of the gauge plate, and ultimately, the interproximal gap. Unfortunately, color-coded gauge plates are problematic in that the practitioner must remember what color represents which thickness. This problem is exacerbated when there are more than three gauge plates, because there are even more color-codes to remember. Alternatively, the practitioner is obligated to review a table provided with the gauge plates, that identifies the color-code and the gauge plate thickness, to estimate the width of the interproximal space. Referring to a table undesirably increases the time needed to perform the dental examination or procedure.

Another problem with some color-coded gauge plates is that the synthetic resin tends to fade and/or break down due to repeated heat and chemical sterilization procedures. This fading in-creases the difficulty in distinguishing one gauge plate from the next, again undesirably increasing the time needed to perform the dental examination or procedure.

Furthermore, color-coded gauge plates can be rendered nearly or completely worthless to practitioners afflicted with color blindness. Color-blind individuals may be unable to distinguish one or several chromatic colors, or may have a complete inability to distinguish the colors of the spectrum, with all objects appearing as shades of gray, black, and white. Thus, some color-blind practitioners may not be able to distinguish one gauge plate from the next.

Repositioning teeth for aesthetic or other reasons is accomplished conventionally by wearing what are commonly referred to as "braces." Braces include a variety of components, such as brackets, archwires, ligatures, and 0-rings. Attaching braces to a patient's teeth is a tedious and time consuming enterprise requiring many meetings with the treating orthodontist. Consequently, conventional orthodontic treatment limits an orthodontist's patient capacity and makes orthodontic treatment quite expensive.

The orthodontics industry is continuously developing new techniques for straightening teeth that are more comfortable and less detectable than traditional braces. One such technique has been the development of disposable and removable retainer-type appliances, known as aligners. Through three-dimensional imaging technology, a sequence of finely calibrated plastic aligners are created. Each aligner is worn for about two weeks and removed only when eating, brushing, and flossing. As each aligner is replaced with the next, the teeth move a small amount until they reach the final alignment prescribed by the orthodontist. This sequence of dental aligners is currently marketed as the Invisalign System by Align Technology, Inc., Santa Clara, Calif.

The process of creating a mechanically-created interproximal gap of a precise width through interproximal reduction is crucial for successful treatment using the Invisalign System in order to accommodate the movement of the teeth.

One common problem experienced near the end of treatment with the Invisalign System is the residual crowding of adjacent teeth due to insufficient interproximal reduction. This residual crowding can impede complete tooth alignment, and generally necessitates further abrasion reduction. Another common problem experienced near the end of treatment with the Invisalign System is the occurrence of residual spaces between adjacent teeth due to excessive interproximal reduction. Residual spaces rarely close on their own, and additional aligners are usually needed, which undesirably increases treatment duration and consequently treatment cost.

Conventional gauge plates of fifty, one hundred and ten, and one hundred and fifty microns in thickness have been developed because the average interproximal distance between teeth is on the order of about 70–92 microns in the case of young men and women. However, in order to accommodate the Invisalign system, the mechanically-created gaps can vary greatly in width between one hundred to nine hundred microns, and even greater, in width. As such, conventional gauge plates are not useful for precisely measuring the wide mechanically-created interproximal gaps, nor the wide variety of gap widths.

SUMMARY OF THE INVENTION

Accordingly, it is an advantage of the present invention that an interproximal gauge and a method for determining a width of an interproximal gap are provided.

It is another advantage of the present invention that an interproximal gauge is provided that readily provides a visual indication of the width of the interproximal gap.

Another advantage of the present invention that an interproximal gauge is provided that can withstand repeated heat and/or chemical sterilization procedures.

Yet another advantage of the present invention is that an interproximal gauge is provided that can determine the width of interproximal gaps having a wide variety of widths.

The above and other advantages of the present invention are carried out in one form by an interproximal gauge for determining a width of a gap between adjacent teeth. The gauge includes a plurality of blades. Each of the blades includes a key portion configured for placement in the gap. The key portion exhibits a predetermined thickness, the predetermined thickness being different for different ones of the blades. A handle adjoins the key portion and includes notches having numerical values representing the predetermined thickness. In operation, one of the plurality of blades is selected having the predetermined thickness that is substantially equivalent to the width, and the notches of the one blade are interpreted to determine the width of the gap.

The above and other advantages of the present invention are carried out in another form by a method for determining a width of a gap between adjacent teeth utilizing an interproximal gauge having a plurality of blades. Each of the blades includes a key portion and a handle adjoining the key portion. The key portion exhibits a predetermined thickness that is different for different ones of the blades, and the handle includes notches having numerical values representing the predetermined thickness. The method calls for placing the key portion of one of the plurality of blades in the gap, determining the predetermined thickness of the key portion is substantially equivalent to the width of the gap, and interpreting the notches to determine the width of the gap.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
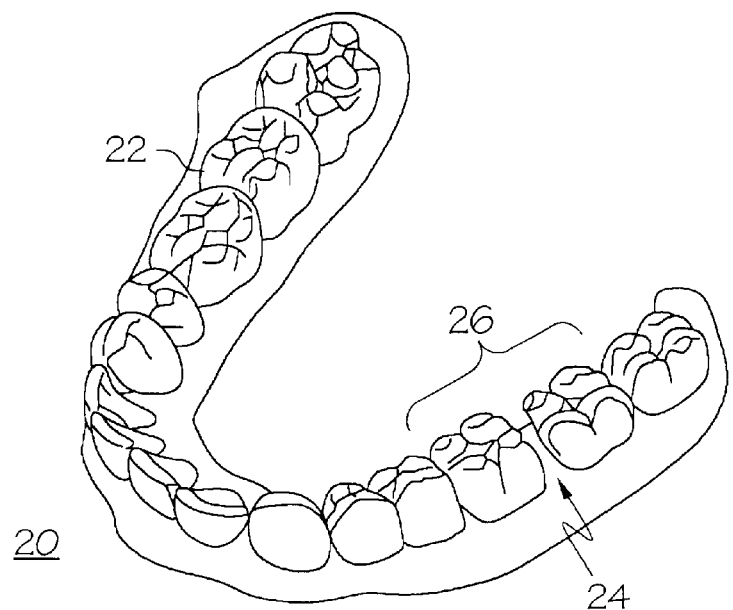
FIG. 1 shows a perspective view of a representative lower jaw.

FIG. 1 shows a perspective view of a representative lower jaw 20. Lower jaw 20 includes fifteen teeth 22. Teeth 22 of jaw 20 may be aligned, rotated, tipped, crowded, and so forth. The patient (not shown) having lower jaw 20, and of course the corresponding upper jaw (not shown), may be undergoing an orthodontic or periodontic procedure. Lower jaw 20 includes an interproximal gap 24 between a pair 26 of adjacent teeth 22, referred to hereinafter as adjacent teeth 26.

Lower jaw 20 includes only one interproximal gap 24 for simplicity of illustration. However, it should be understood, that lower jaw 20 and the corresponding upper jaw may have additional gaps 24 between other adjacent teeth 22. In addition, these additional gaps 24 may be of a variety of widths ranging from 100–900 microns or greater.

Figure 2:
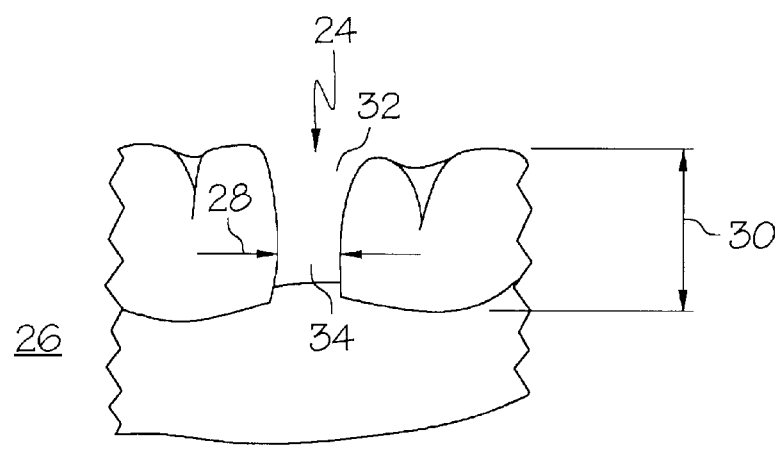
FIG. 2 shows a side view of an interproximal gap between adjacent teach in the jaw of FIG. 1.

Referring to FIG. 2 in connection with FIG. 1, FIG. 2 shows a side view of adjacent teeth 26 of jaw 20 and interproximal gap 24 located between adjacent teeth 26. Interproximal gap 24 is a space between adjacent teeth 26 that may be naturally-occurring or mechanically-created. In an exemplary embodiment, gap 24 was mechanically-created during an interproximal reduction process by a practitioner using high-speed instrumentation, manual abrasion strips, or a combination of both. Gap 24 may have been created in preparation for treatment using a series of incremental position adjustment appliances, such as the Invisalign System aligners (discussed above).

Gap 24 exhibits a gap width 28 and a gap height 30. The present invention accurately measures gap width 28. Following an interproximal reduction process, gap 24 should ideally exhibit a uniform gap width 28 at a top 32 of gap 24 relative to a bottom 34 of gap 24, i.e., gap width 28 should be constant along gap height 30. The present invention can be utilized to evaluate the uniformity of gap width 28 along throughout gap height 30.

Figure 3:
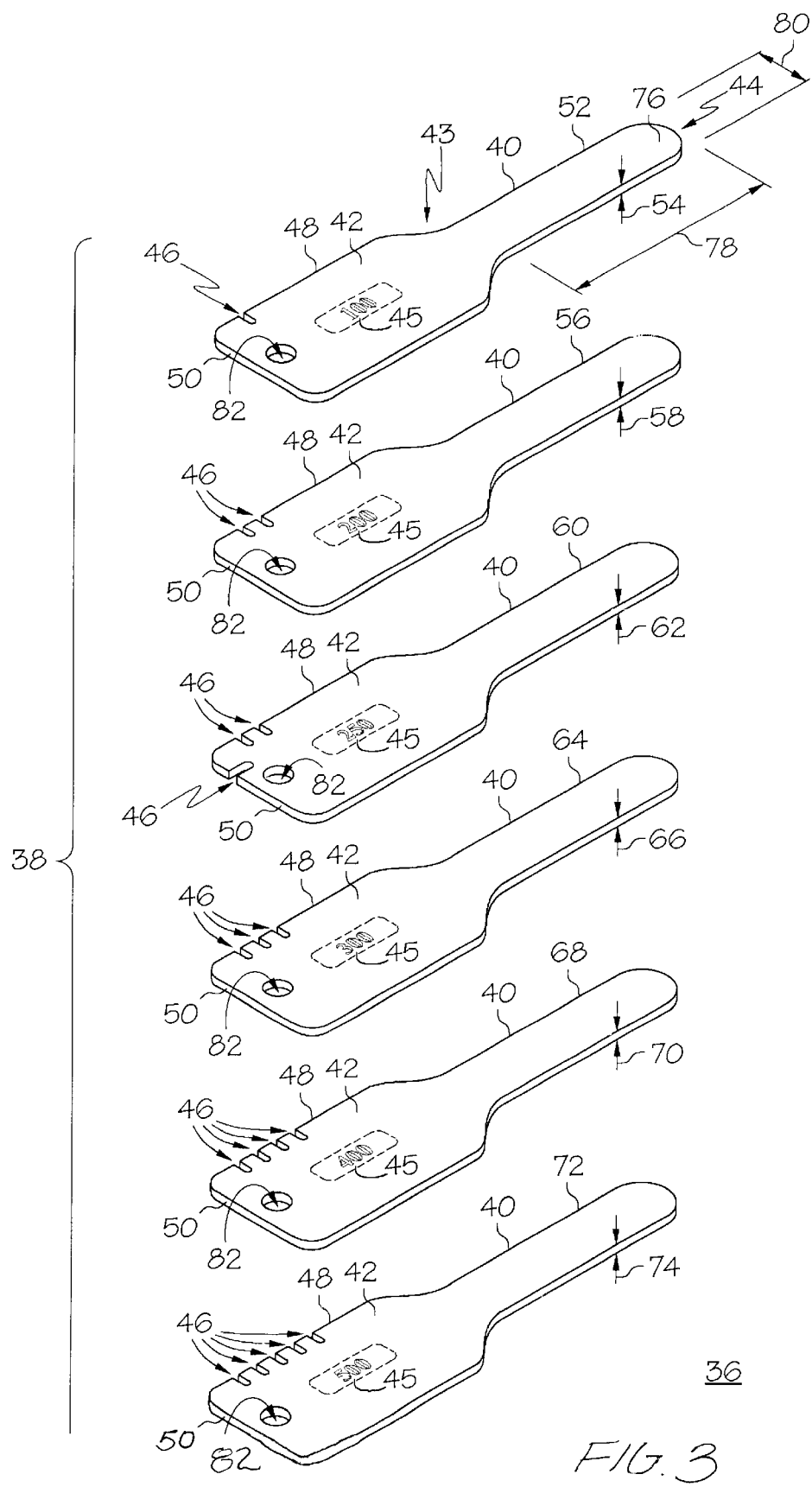
FIG. 3 shows a perspective view of an interproximal gauge in accordance with a preferred embodiment of the present invention.

FIG. 3 shows a perspective view of an interproximal gauge 36 in accordance with a preferred embodiment of the present invention. Interproximal gauge 36 is utilized to determine width 28 (FIG. 2) of gap 24 (FIG. 2) between adjacent teeth 26 (FIG. 2) in connection with orthodontic, periodontic, and other dental treatment procedures. For example, interproximal gauge 36 can be used to accurately measure the amount of space that is created between adjacent teeth 26 by the reduction of the enamel surface of either or both adjacent test 26.

Interproximal gauge 36 provides means by which a practitioner can reproduce the precise amount of enamel reduction called for by the changes in the digital images produced by the three-dimensional imaging technology of the Invisalign System to assist in the precise movement of teeth 22 (FIG. 1) with the Invisalign System aligners.

Interproximal gauge 36 includes a series of blades 38. Each of blades 38 includes a key portion 40 configured for placement in gap 28 (FIG. 1) and a handle 42 adjoining key portion 40. In particular, key portion 40 includes a first end 43 that adjoins handle 42 and a second end 44 opposing first end 43. Second end 44 is outwardly rounded so that there are no sharp corners that could cause lacerations, scratches, or other injury to tongue, gums, and other tender tissues of the mouth when key portion 40 is placed in gap 24.

Key portion 40 and handle 42 are formed as an integral unit from a heat resistant material. In a preferred embodiment, key portion 40 and handle 42 are constructed from a sheet metal, such as stainless steel. Stainless steel is preferred due to its resistance to rust and attack from chemicals. In addition, stainless steel does not suffer from degradation due to repeated heat and/or chemical sterilization procedures. Thus, each of blades 38 retains an original visual appearance during repeated sterilization procedures so that etchings 45 or any other distinguishing markings are not worn off blades 38. Those skilled in the art will recognize that key portion 40 and handle 42 may be constructed as a unit from other suitable materials, such as heat resistant plastics, ceramics, and other metal alloys.

Key portion 40 exhibits a predetermined thickness that is different for different ones of blades 38, and handle 42 includes notches 46 having n representing the predetermined thickness (discussed below). Notches 46 are positioned on a first edge 48 of handle 42. In addition, an additional one of notches 46 may be positioned on a second edge 50 of handle 42.

In a preferred embodiment, each of notches 46 positioned along first edge 48 has a first numerical value of one hundred microns. Notch 46 positioned on second edge 50 has a second numerical value of fifty microns. The predetermined thickness of one blades 38 may be determined by interpreting the numerical values of each of notches 46 positioned on handle 42 relative to their location on first and second edges 48 and 50, respectively. In particular, when blades 38 have more one of notches 46 positioned on handle 42, the numerical values of each of notches 46 are summed to determine the predetermined width.

In a preferred embodiment, a first one of blades 38, i.e., a first blade 52, of interproximal gauge 36 exhibits a first predetermined thickness 54. First predetermined thickness 54 is represented by one of notches 46 positioned on first edge 48 of handle 42. Accordingly, first predetermined thickness 54 of first blade 52 is one hundred microns. A second one of blades 38, i.e., a second blade 56 of gauge 36 exhibits a second predetermined thickness 58 represented by a pair of notches 46 positioned on first edge 48. Thus, second predetermined thickness 58 is two hundred microns. A third one of blades 38, i.e., a third blade 60 of gauge 36 exhibits a third predetermined thickness 62 represented by a pair of notches 46 positioned on first edge 48.and-a single one of notches 46 positioned on second edge 50. As such, a summation of first and second numerical values of notches 46 yield third predetermined thickness 62 of two hundred and fifty microns. Similarly, a fourth one of blades 38, i.e., fourth blade 64 exhibits a fourth predetermined thickness 66 of three hundred microns. A fifth one of blades 38, i.e., a fifth blade 68 exhibits a fifth predetermined thickness 70 of four hundred microns, and a sixth one of blades 38, i.e. a sixth blade 72 exhibits a sixth predetermined thickness 74 of five hundred microns.

For each of blades 38, key portion 40 is a substantially planar surface 76 characterized by a length 78 and a height 80, and the corresponding predetermined thickness is substantially constant along key portion 40. With particular reference to first blade 52, first predetermined thickness 54 of first blade 52 is substantially constant along length 78 and height 80 of key portion 40. In addition, height 80 of planar surface 76 is configured to be greater than gap height 30 (FIG. 2) of teeth 22. Height 80 is advantageously greater than gap height 30 so that the uniformity of width 28 may be evaluated from top 32 (FIG. 2) to bottom 34 (FIG. 2) of gap 24.

In a preferred embodiment, interproximal gauge 36 includes first, second, third, fourth, fifth, and sixth blades 52, 56, 60, 64, 68, and 72 having a range of predetermined thicknesses from one hundred microns through five hundred microns for determining width 28 (FIG. 2) of interproximal gap 24 (FIG. 2) that was created to accommodate movement of teeth 22 (FIG. 1) using an aligner, such as Invisalign System. However, it should be understood that in an alternative embodiment, interproximal gauge 36 may include additional blades 38 or blades 38 of different predetermined thickness than those described above to better accommodate the dental procedure being undertaken.

For example, interproximal gauge may be employed to measure a naturally occurring gap 24 (FIG. 1) in a young person undergoing-a conventional orthodontic procedure. In such a situation, gauge 36 may include one of blades 38 having key portion 40 exhibiting a predetermined thickness of fifty microns. As such, this additional blade would have a single one of notches 46 positioned along second edge 50, and none of notches 46 along first edge 48.

In addition, first, second, third, fourth, fifth, and sixth blades 52, 56, 60, 64, 68, and 72 are shown as separate units for simplicity of illustration and so that separate blades may be readily selected for placement in gap 24 (FIG. 2). As such, first, second, third, fourth, fifth, and sixth blades 52, 56, 60, 64, 68, and 72 may be stored in a container, or box, having slots into which each of first, second, third, fourth, fifth, and sixth blades 52, 56, 60, 64, 68, and 72 are placed when not in use. Alternatively, first, second, third, fourth, fifth, and sixth blades 52, 56, 60, 64, 68, and 72 may be interconnected using a key ring structure (not shown) directed through each of holes 80 in handle 42.

Figure 4:
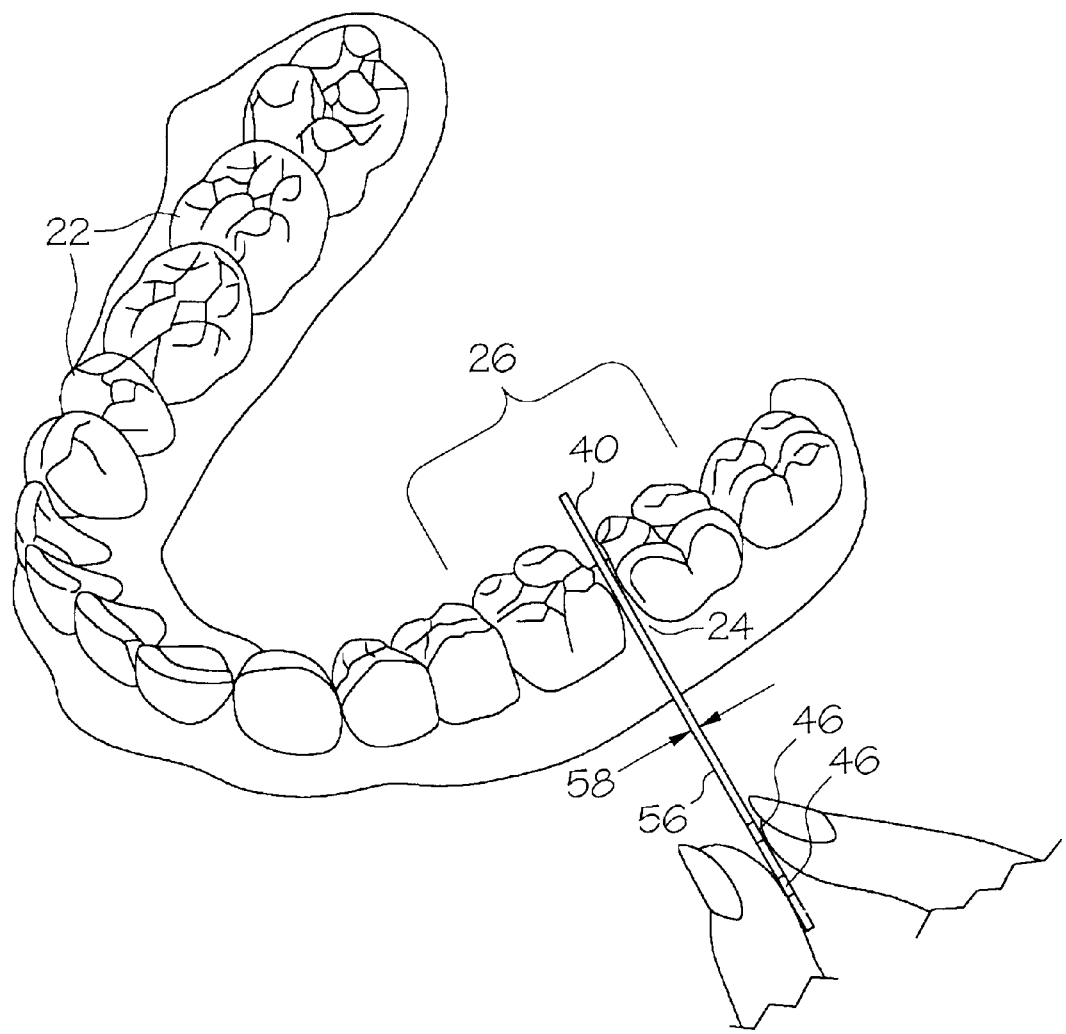
FIG. 4 shows a perspective view of interproximal gauge in use.

FIG. 4 shows a perspective view of interproximal gauge 36 (FIG. 3) in use. In particular, key portion 40 of one of first, second, third, fourth, fifth, and sixth blades 52, 56, 60, 64, 68, and 72 is placed in gap 24. In practice, successive ones of blades 38 are inserted into gap 24 in order of predetermined thickness, from first blade 52 (FIG. 3) to sixth blade 72 (FIG. 3)., until the succeeding one of blades 38 cannot be inserted therein.

By way of illustration, key portion 40 of second blade 56 is placed in interproximal gap 24. When the practitioner determines that second predetermined thickness 58 is substantially equivalent to gap width 28 (FIG. 2), notches 46 are interpreted to determine width 28 of gap 24. That is, the practitioner merely ascertains a quantity of notches 46 on first edge 48 of handle 42 and/or notches 46 on second edge 50 of handle 42 and sums the numerical values assigned to notches 46 to discern width 28.

Alternatively, when the practitioner determines that second predetermined thickness 58 is not substantially equivalent to gap width 28, the practitioner selects succeeding ones of blades 38 (FIG. 3) and places the succeeding ones of blades 38 in gap 24 until one of blades 38 is determined to have a predetermined thickness substantially equivalent to width 28. Notches 46 on the one of blades 38 determined to have a predetermined thickness substantially equivalent to width 28 are subsequently interpreted to discern width 28.

On occasion, the practitioner may determine that width 28 of interproximal gap 24 is wider than the thickest one of blades 38, that is, width 28 is greater than sixth blade 72 (FIG. 3) having a predetermined thickness 74 (FIG. 3) of five hundred microns. Such a situation may intentionally arise when gap 24 is mechanically-created during an interproximal reduction process.

When sixth predetermined thickness 74 is less than width 28, the practitioner can then select two of blades 38 and hold them in adjacent relationship, i.e., such that respective planar surfaces 76 (FIG. 3) are parallel and the selected two of blades 38 abut one another, and place the selected two of blades 38 in gap 24. For example, the practitioner may place both first blade 52 (FIG. 3) having first predetermined thickness 54 of one hundred microns and sixth blade 72 having sixth predetermined thickness 74 of five hundred microns to determine whether width 28 is six hundred microns. Thus, pairs, triplets, and so forth of blades 38 may be combined to determine width 28 greater than five hundred microns.

For optimal results in a reduction process, when gap 24 is mechanically-created during an interproximal reduction process, width 28 of gap 24 should be relatively constant from top 32 (FIG. 2) to bottom 34 (FIG. 2) of gap height 30 (FIG. 2). That is, width 28 should be uniform from top 32 to bottom 34. This uniformity is evaluated by rocking key portion 40 of one of blades 38, for example, second predetermined blade 56, in gap 24. Excessive rocking at either top 32 or bottom 24 of gap height 30, relative to the other of gap height 30, indicates that width 28 of gap 24 is not uniform and should be corrected in the reduction process.

In summary, the present invention teaches of an interproximal gauge and a method for accurately determining a width of an interproximal gap. The notches on the handle of each of the blades of the interproximal gauge readily provide a visual indication of the width of the interproximal gap, even following repeated heat and/or chemical sterilization procedures. More specifically, the stainless steel, single unit construction can withstand the repeated sterilization procedures without loss of the original visual appearance. In addition, a wide variety of widths of interproximal gaps can be precisely determined using individual blades or by combining two or more blades.

Although the preferred embodiments of the invention have been illustrated and described in detail, it will be readily apparent to those skilled in the art that various modifications may be made therein without departing from the spirit of the invention or from the scope of the appended claims.

What is claimed is:

1. An interproximal gauge for determining a width of a gap between adjacent teeth, said gauge comprising:
    a plurality of blades, each of said blades including:
        a key portion configured for placement in said gap, said key portion exhibiting a predetermined thickness, said predetermined thickness being different for different ones of said blades; and
        a handle adjoining said key portion, said handle including notches having numerical values representing said predetermined thickness; wherein
    one of said plurality of blades is selected having said predetermined thickness that is substantially equivalent to said width, and said notches of said one blade are interpreted to determine said width of said gap.

2. An interproximal gauge as claimed in claim 1 wherein said predetermined thickness is substantially constant along a length and height of said key portion.

3. An interproximal gauge as claimed in claim 1 wherein said gap exhibits a gap height, and said key portion includes a substantially planar surface, said planar surface exhibiting height configured to be greater than said gap height.

4. An interproximal gauge as claimed in claim 1 wherein said key portion includes:
    a first end adjoining said handle; and
    a second end opposing said first end, said second end being outwardly rounded.

5. A interproximal gauge as claimed in claim 1 wherein said notches are positioned along an edge of said handle.

6. An interproximal gauge as claimed in claim 1 wherein each of said plurality of blades includes at least one of said notches positioned along a first edge of said handle; and said predetermined thickness of said key portion of said each of said blades is represented by a summation of said numerical values for each of said at least one of said notches positioned along said first edge of said handle.

7. An interproximal gauge as claimed in claim 6 wherein said numerical values for said each of said notches positioned along said first edge of said handle is one hundred microns.

8. An interproximal gauge as claimed in claim 6 wherein said numerical values are first numerical values, one of said plurality of blades further includes one of said notches positioned along a second edge of said handle, said one of said notches having a second numerical value, and said predetermined thickness of said one of said blades is represented by said summation of said first numerical values for said each of said notches positioned along said first edge of said handle with said second numerical value of said one of said notches positioned along said second edge of said handle.

9. An interproximal gauge as claimed in claim 8 wherein:
    said first numerical values for said each of said notches positioned along said first edge of said handle is one hundred microns; and
    said second numerical value for said one of said notches positioned along said second edge of said handle is fifty microns.

10. An interproximal gauge as claimed in claim 1 wherein said key portion and said handle are formed as a unit from a heat resistant material capable of retaining an original visual appearance during a heat sterilization process.

11. An interproximal gauge as claimed in claim 1 wherein key portion and said handle are formed as a unit from stainless steel.

12. A method for determining a width of a gap between adjacent teeth utilizing an interproximal gauge having a plurality of blades, each of said blades including a key portion and a handle adjoining said key portion, said key portion exhibiting a predetermined thickness that is different for different ones of said blades, and said handle including notches having numerical values representing said predetermined thickness, said method comprising:
    placing said key portion of one of said plurality of blades in said gap;
    determining said predetermined thickness of said key portion is substantially equivalent to said width of said gap; and
    interpreting said notches to determine said width of said gap.

13. A method as claimed in claim 12 further comprising:
    determining said predetermined thickness of said key portion is different from said width of said gap;
    selecting others of said blades;
    repeating said placing operation using said others of said blades until said predetermined thickness of said key portion of one of said others of said blades is substantially equivalent to said width of said gap; and
    interpreting said notches of said one of said others of said blades to determine said width of said gap.

14. A method as claimed in claim 12 wherein said interpreting operation comprises:
    ascertaining a quantity of said notches positioned along said handle; and
    summing said numerical values for each of said notches on said handle of said one of said plurality of blades to discern said predetermined thickness.

15. A method as claimed in claim 12 wherein said one of said plurality of blades includes at least one of said notches positioned along a first edge of said handle, said at least one of said notches representing one hundred microns.

16. A method as claimed in claim 15 wherein said one of said plurality of blades further includes a second one of said notches positioned along a second edge of said handle, said second one of said notches representing fifty microns.

17. A method as claimed in claim 12 further comprising:
    determining said predetermined thickness of said key portion is different from said width of said gap;
    selecting another of said plurality of blades having said key portion that exhibits a greatest of said predetermined thickness;
    determining said greatest predetermined thickness to be less than said width of said gap; and placing at least two of said key portions of at least two of said plurality of blades in adjacent relationship in said gap;

determining said predetermined thickness of said at least two of said key portions is substantially equivalent to said width of said gap; and interpreting said notches in said handle of said at least two of said plurality of said blades to determine said width of said gap.

18. A method as claimed in claim 12 wherein said gap exhibits a gap height, said key portion includes a substantially planar surface, said planar surface exhibiting a height configured to be greater than said gap height, and said method further comprises rocking said key portion in said gap to evaluate a uniformity of said width throughout said gap height.

19. An interproximal gauge for determining a width of a gap between adjacent teeth, said gauge comprising:

a first blade, a second blade, and a third blade, each of said first, second, and third blades including a key portion configured for placement in said gap and a handle integral with said key portion, said handle having a first edge and a second edge, and said handle exhibiting notches on at least one of said first and second edges; wherein said key portion of said first blade exhibits a first predetermined thickness, and said handle of said first blade includes one of said notches positioned on said first edge, said one of said notches having a first one of said numerical values representing said first predetermined thickness;

said key portion of said second blade exhibits a second predetermined thickness, and said handle of said second blade includes at least two of said notches positioned on said first edge, each of said at least two of said notches having said first one of said numerical values, and a summation of said first numerical value for said each of said at least two of said notches represents said second predetermined thickness;

said key portion of said third blade exhibits a third predetermined thickness, and said handle of said third blade includes a pair of said notches positioned on said first edge and a single one of said notches positioned on said second edge, each of said pair of said notches having said first numerical value and said single one of said notches having a second one of said numerical values, and a summation of said first numerical value for said each of said pair of said notches with said second numerical value represents said third predetermined thickness; and one of said first, second, and third blades is selected having a corresponding one of said first, second, and third predetermined thicknesses that is substantially equivalent to said width, said notches of said one selected blade being interpreted to determine said width of said gap.

20. An interproximal gauge as claimed in claim 19 wherein:

said first numerical value of said notches positioned along said first edge of said handle is one hundred microns; and said second numerical value of said single one of said notches positioned along said second edge of said handle is fifty microns.

* * * * *